United States Patent
Huang et al.

(10) Patent No.: US 11,478,411 B2
(45) Date of Patent: Oct. 25, 2022

(54) USE OF CHELATING AGENTS FOR IMPROVING COLOR STABILITY OF RESORCINOL

(71) Applicant: Conopco, Inc., Englewood Cliffs, NJ (US)

(72) Inventors: Lei Huang, Trumbull, CT (US); Teanoosh Moaddel, Watertown, CT (US)

(73) Assignee: Conopco, Inc., Englewood Cliffs, NJ (US)

( * ) Notice: Subject to any disclaimer, the term of this patent is extended or adjusted under 35 U.S.C. 154(b) by 19 days.

(21) Appl. No.: 16/467,572

(22) PCT Filed: Nov. 27, 2017

(86) PCT No.: PCT/EP2017/080503
§ 371 (c)(1),
(2) Date: Jun. 7, 2019

(87) PCT Pub. No.: WO2018/114232
PCT Pub. Date: Jun. 28, 2018

(65) Prior Publication Data
US 2019/0358140 A1    Nov. 28, 2019

(30) Foreign Application Priority Data
Dec. 21, 2016 (EP) .................................. 16205674

(51) Int. Cl.
*A61K 8/44* (2006.01)
*A61Q 17/04* (2006.01)
*A61K 8/34* (2006.01)
*A61K 8/67* (2006.01)
*A61K 8/36* (2006.01)
*A61K 8/37* (2006.01)
*A61K 8/29* (2006.01)
*A61K 8/06* (2006.01)

(52) U.S. Cl.
CPC .................. *A61K 8/44* (2013.01); *A61K 8/06* (2013.01); *A61K 8/29* (2013.01); *A61K 8/345* (2013.01); *A61K 8/347* (2013.01); *A61K 8/361* (2013.01); *A61K 8/37* (2013.01); *A61K 8/673* (2013.01); *A61K 8/675* (2013.01); *A61K 8/678* (2013.01); *A61Q 17/04* (2013.01)

(58) Field of Classification Search
CPC ... A61K 8/44; A61K 8/06; A61K 8/29; A61K 8/345; A61K 8/347; A61K 8/361; A61K 8/37; A61K 8/673; A61K 8/675; A61K 8/678; A61Q 17/04
See application file for complete search history.

(56) References Cited

U.S. PATENT DOCUMENTS

| | | | |
|---|---|---|---|
| 3,265,571 A | 8/1966 | Krezanoski | |
| 5,843,193 A * | 12/1998 | Hawkins | A61Q 5/10 8/408 |
| 6,277,154 B1 | 8/2001 | Lorenz | |
| 6,869,598 B2 | 3/2005 | Love et al. | |
| 6,863,897 B2 | 8/2005 | Love et al. | |
| 7,018,426 B2 * | 3/2006 | Javet | A61K 8/494 548/302.7 |
| 2003/0180234 A1 | 9/2003 | Love et al. | |
| 2003/0185773 A1 | 10/2003 | Love et al. | |
| 2004/0109832 A1 | 6/2004 | Harichian et al. | |
| 2006/0210497 A1 | 9/2006 | Harichian et al. | |
| 2008/0305059 A1 | 12/2008 | Chaudhuri | |

FOREIGN PATENT DOCUMENTS

| | | |
|---|---|---|
| CN | 1638724 | 7/2005 |
| CN | 1642512 | 7/2005 |
| CN | 101175711 | 5/2008 |
| CN | 105188653 | 12/2015 |
| DE | 102004025281 | 12/2005 |
| EP | 0965324 A1 * | 12/1999 |
| EP | 2292208 | 3/2011 |
| JP | 61236709 | 10/1986 |
| JP | 5263940 | 5/1999 |
| JP | 11199454 | 7/1999 |
| KR | 20040008313 | 1/2004 |
| WO | WO2014111563 | 7/2014 |
| WO | WO2016016148 | 2/2016 |

OTHER PUBLICATIONS

IPRP2 in PCTEP2017080503.
Search Report and Written Opinion in PCTEP2017080503; dated Feb. 9, 2018.
Search Report and Written Opinion in EP16205674; dated Mar. 2, 2017.
Notice of Opposition in EP17811246 (EP3558224); Feb. 2, 2021; with English manual translation.
Resorcin; Wikipedia; 2021; in English and German, pp. 1-15.
Perubalsam; Wikipedia; 2021; with German original and English machine translation, pp. 1-6.
Data Sheet for Lanette O; OleoChemicals, Cognis; Oct. 1, 2001; pp. 1-2.
Arthur E. Martell; Chelates of Ascorbic Acid, in Advances in Chemistry; 1982; pp. 153-178 (+plus 6 cover pages, total 32 pages); 200.
Comparative test results in PCTEP2017080503; Unilever; Sep. 13, 2018; 1-4.

* cited by examiner

*Primary Examiner* — Hong Yu
(74) *Attorney, Agent, or Firm* — Stephanie S. DelPonte

(57) ABSTRACT

Cosmetic compositions are widely used to obtain certain benefits like e.g. anti-aging, skin lightening and moisturizing effect. These benefits are delivered by benefit agents (actives) like e.g. anti-oxidants, hyaluronic acid and resorcinol, pheynylethyl resorcinol and 4-alkyl substituted resorcinol. However, these actives have a certain shelf life beyond which they tend to degrade in terms of chemical activity and/or their color stability. The present invention discloses a novel process to prepare cosmetic compositions that improved color stability of resorcinol, pheynylethyl resorcinol and 4-alkyl substituted resorcinol and compositions comprising such actives when prepared as per said process.

10 Claims, No Drawings

USE OF CHELATING AGENTS FOR IMPROVING COLOR STABILITY OF RESORCINOL

FIELD OF THE INVENTION

The present invention relates to stability of actives in cosmetic compositions. In particular, the present invention relates to color stability of resorcinol, phenylethyl resorcinol (PER) and 4-alkyl substituted resorcinol in cosmetic compositions.

BACKGROUND OF THE INVENTION

Cosmetic compositions of various kinds are widely used by consumers. Cosmetic compositions in the form of lotions, creams, gels and masks are used by consumers to obtain certain benefits like e.g. anti-aging, skin lightening and moisturizing effect. Much of these benefits are delivered by actives like e.g. anti-oxidants, hyaluronic acid and 4-alkyl substituted resorcinol like e.g. 4-ethyl resorcinol (ER) and 4-hexyl resorcinol (HR).

However, these actives tend to have a certain shelf life beyond which they tend to undergo degradation in terms of their activity (chemical stability) and/or their color appearance. For example, 4-alkyl substituted resorcinol are known for their good skin lightening capacity. However, they tend to suffer the stability issue, in particular, color stability. Particularly in the field of cosmetics, color stability is closely associated with consumers' perception of quality and functionality of products. Therefore, color stability of actives like e.g. resorcinol, PER and 4-alkyl substituted resorcinol has been a topic of research for quite some time.

Nitrogen processing, special packaging and physical color matching have been used to address the color stability of resorcinol and 4-alkyl substituted resorcinol.

US2008305059 (Sytheon Ltd) discloses usage of highly purified hexyl resorcinol to address the color stability issue that arises from impurities like presence of other undesired phenols and polyphenols in commercial grade $C_2$-$C_{12}$ alkyl resorcinol. US2008305059 further cites that color stability issue is more severe with straight chain and branched alkyl substituted resorcinol derivatives and further mentions that, many if not all, phenol based skin lightening agents irrespective of their synthetic or natural origin, tend to suffer color instability due to their susceptibility to air and/or UV oxidation.

U.S. Pat. No. 6,863,897 (Unilever) discloses use of micronized metal oxides like e.g. titanium oxide and zinc oxide, to provide color stability to 4-substituted resorcinol. Further, U.S. Pat. No. 6,863,897 and US2003185773 (Unilever) disclose that resorcinol or its derivatives and chelating agents are present in different phases in the process of manufacturing formulations disclosed therein. For example, resorcinol derivatives are present in phase D whereas chelating agents, i.e. ethylene diamine tetraacetic acid (EDTA), is present in phase B of formulation making process.

U.S. Pat. No. 3,265,571 (Bares Hind) discloses compositions containing resorcinol and EDTA and discloses a method by which the composition is prepared where resorcinol is not combined with EDTA first. U.S. Pat. No. 3,265,571 further discloses that EDTA chelates metals that would cause the normal development of color in the presence of salicylic acid and/or resorcinol.

JP S61 236709 (Shiseido Co) discloses a method to address drawbacks of instability of resorcinol in formulation based on clay minerals and/or inorganic powder. The compositions disclosed therein are prepared where edetate is added to a pre-mix containing clay, i.e. bentonite and kaolin, zinc, glycerin, water and resorcinol.

The methods tried thus far to address color stability, seem to be either associated with complex and/or cost ineffective processing or requirement of special compounds that are not always preferred. Therefore, stabilization of actives, particularly of resorcinol, PER and 4-alkyl substituted resorcinol, in cosmetic compositions, still remains a topic of interest.

It has now been found that combining a compound selected from resorcinol, PER, 4-alkyl substituted resorcinol and mixtures thereof with chelating agents in a specific way delivered color stability to resorcinol, PER and 4-alkyl substituted resorcinol.

SUMMARY OF THE INVENTION

In a first aspect, the present invention provides a process for preparing a composition comprising
i. a compound selected from resorcinol, phenylethyl resorcinol, 4-alkyl substituted resorcinol and mixtures thereof,
ii. a chelating agent, and;
iii. a cosmetically acceptable base comprising a water phase and an oil phase wherein, the process comprises the steps of
(a) combining a compound selected from resorcinol, phenylethyl resorcinol, 4-alkyl substituted resorcinol and mixtures thereof with a chelating agent in water,
(b) preparing a water phase and an oil phase,
(c) combining the water phase and the oil phase to prepare cosmetically acceptable base, and;
(d) combining the adduct obtained in step (a) with the cosmetically acceptable base of step (c)

DETAILED DESCRIPTION OF THE INVENTION

Unless specified otherwise, amounts as used herein are expressed in percentage by weight based on total weight of the composition and is abbreviated as "wt %".

The use of any and all examples or exemplary language e.g. "such as" provided herein is intended merely to better illuminate the invention and does not in any way limit the scope of the invention otherwise claimed.

The composition prepared as per the process of the present invention comprises
i. a compound selected from resorcinol, PER, 4-alkyl substituted resorcinol and mixtures thereof,
ii. a chelating agent, and;
iii. a cosmetically acceptable base.

Resorcinol, PER and 4-Alkyl Substituted Resorcinol

The composition prepared as per the process of the present invention comprises a compound selected from resorcinol, PER, 4-alkyl substituted resorcinol and mixtures thereof. The alkyl group in 4-alkyl substituted resorcinol can be straight chain alkyl or branched chain alkyl. For example, the alkyl group can be straight chain alkyl like e.g. in case of 4-propyl resorcinol or it can be branched chain alkyl like e.g. in case of 4-isopropyl resorcinol (IPR). Illustrative examples of 4-alkyl substituted resorcinol include 4-methyl resorcinol, ER, 4-propyl resorcinol, IPR, 4-butyl resorcinol, 4-pentyl resorcinol, HR, 4-heptyl resorcinol, 4-octyl resorcinol and mixtures thereof. Preferred 4-alkyl substituted resorcinol are any one of ER and HR.

It will be understood that the composition may comprise a combination of one or more compounds selected from resorcinol, PER and 4-alkyl substituted resorcinol. For example, the composition may comprise one or more 4-alkyl substituted resorcinol in presence or absence of resorcinol. Preferably, the composition comprises one compound selected from resorcinol, PER, 4-alkyl substituted resorcinol. The total amount of resorcinol, PER, 4-alkyl substituted resorcinol and mixtures thereof in the composition is preferably in the range from 0.01 to 10 wt %, more preferably from 0.1 to 5 wt % and most preferably from 0.25 to 3 wt %.

Chelating Agents

Chelating agents are well known in the art and are frequently used in cosmetic compositions.

Illustrative examples of chelating agents include EDTA, ethylene diamine disuccinic acid (EDDS), pentasodium diethylenetriaminepentaacetate, trisodium N-(hydroxyethyl)-ethylenediaminetracetate, an acid form of EDTA, sodium thiocynate, trisodium salt of methylglycinediacetic acid, tetrasodium glutamate diacetate and phytic acid. Preferred chelating agents are EDTA, EDDS and mixtures thereof.

The composition according to the present invention may comprise one or more chelating agents, preferably one. The total amount of chelating agent in the composition preferably is in the range from 0.001 to 10 wt %, more preferably from 0.01 to 5 wt %, further more preferably from 0.05 to 3 wt % and most preferably from 0.1 to 2 wt %.

Illustrative combinations of resorcinol compounds and chelating agents include HR+EDTA, ER+EDTA, PER+EDTA, IPR+EDTA, ER+EDDS, PER+EDDS, IPR+EDDS. Preferred combinations are HR+EDTA, ER+EDTA and ER+EDDS.

The process of the present invention does not comprise a combination of HR+EDDS. That is to say when HR is used as a resorcinol compound, a chelating agent other than EDDS is used.

Cosmetically Acceptable Base

The composition comprises a cosmetically acceptable base to act as a diluent, dispersant or carrier for other materials present in the composition, so as to facilitate their distribution when the composition is applied to the skin.

The cosmetically acceptable base as per the present invention is an emulsion comprising a water phase and an oil phase and includes oil-in-water and water-in-oil emulsions. A preferred type of emulsion is oil-in-water.

The water phase, if required, may be comprised only of water. The amount of water may range from 1 to 99 wt %, preferably from 5 to 90 wt %, more preferably from 35 to 85 wt %, and most preferably from 40 to 75 wt %.

The oil phase may comprise fatty acids having from 10 to 30 carbon atoms and salts thereof. Illustrative examples of fatty acids having from 10 to 30 carbon atoms include pelargonic, lauric, myristic, palmitic, stearic, isostearic, oleic, linoleic, arachidic, behenic or erucic acid, and mixtures thereof. An illustrative example of salts of fatty acid is potassium stearate.

The composition preferably comprises from 5 to 25 wt %, more preferably from 7 to 20 wt %, further more preferably 9 to 17 wt % and most preferably 10 to 15 wt % of fatty acids and/or its salts.

The cosmetically acceptable base may further comprise liquid or solid emollients, solvents, humectants, thickeners and powders, skin penetration enhancers or mixtures thereof.

Illustrative examples of emollients include stearyl alcohol, glyceryl monoricinoleate, mink oil, isopropyl isostearate, stearic acid, isobutyl palmitate, isocetyl stearate, oleyl alcohol, isopropyl laurate, hexyl laurate, decyl oleate, octadecan-2-ol, isocetyl alcohol, eicosanyl alcohol, cetyl palmitate, silicone oils such as dimethylpolysiloxane, din-butyl sebacate, isopropyl myristate, isopropyl palmitate, isopropyl stearate, butyl stearate, polyethylene glycol, triethylene glycol, lanolin, cocoa butter, corn oil, cotton seed oil, olive oil, palm kernel oil, rape seed oil, safflower seed oil, evening primrose oil, soybean oil, sunflower seed oil, avocado oil, sesame seed oil, coconut oil, *arachis* oil, castor oil, acetylated lanolin alcohols, petroleum jelly, mineral oil, butyl myristate, isostearic acid, palmitic acid, isopropyl linoleate, lauryl lactate, myristyl lactate, decyl oleate and myristyl myristate.

Illustrative examples of solvents include ethyl alcohol, isopropanol, acetone, ethylene glycol monoethyl ether, diethylene glycol monobutyl ether and diethylene glycol monoethyl ether.

Illustrative examples of powders include chalk, talc, fullers earth, kaolin, starch, gums, colloidal silica sodium polyacrylate, tetra alkyl and/or trialkyl aryl ammonium smectites, chemically modified magnesium aluminium silicate, organically modified montmorillonite clay, hydrated aluminium silicate, fumed silica, carboxyvinyl polymer, sodium carboxymethyl cellulose and ethylene glycol monostearate.

Compounds that are believed to enhance skin penetration, like dimethyl sulfoxide, may also be used as cosmetically acceptable base.

Preferred cosmetically acceptable base comprises water, stearic acid and potassium stearate.

The cosmetically acceptable base is usually present from 10 to 99.9 wt %, preferably from 50 to 99 wt %, more preferably from 60 to 99 wt %, further more preferably from 70 to 99 wt %, even more preferably from 80 to 99 wt % and most preferably from 90 to 99 wt %.

Vitamins

The composition may further comprise vitamins like e.g. vitamin C, vitamin B2, vitamin B3, vitamin B6, vitamin E, folic acid, biotin, vitamin D and vitamin K. In addition, derivatives of vitamins like e.g. derivative of vitamin E like e.g. tocopheryl acetate or derivative of vitamin C like e.g. ascorbyl tetraisopalmitate and derivative of vitamin A like e.g. vitamin A palmitate, may also be present in the composition. Preferred vitamins are vitamin E or its derivatives like e.g. tocopheryl acetate and vitamin B3.

Total amount of vitamins that could be present in the composition may range from 0 to 10 wt %, preferably from 0.01 to 7 wt %, more preferably from 0.1 to 5 wt % and most preferably from 1 to 3 wt %.

The composition may further comprise polyols that enhance the solubility of resorcinol, PER, 4-alkyl substituted resorcinol for example, solubility of HR in water. Illustrative examples of polyols include glycerol, ethylene glycol, propylene glycol butylene glycol, polypropylene glycol and polyethylene glycol. Preferred polyol is glycerol, butylene glycol, propylene glycol or mixtures thereof.

The present invention comprises polyols in an amount ranging from 0.01 to 10 wt %, preferably from 0.1 to 5 wt %, more preferably from 1 to 3 wt %.

Emulsifiers

Emulsifiers may be present in the composition of the present invention. The emulsifiers selected can be of nonionic, anionic, cationic and amphoteric in nature.

Illustrative examples of nonionic emulsifiers include C10-C20 branched or linear fatty alcohol like e.g. cetyl alcohol and behenyl alcohol or acid hydrophobe condensed with from about 2 to about 100 moles of ethylene oxide or propylene oxide per mole of hydrophobe, C2-C10 alkyl phenols condensed with from 2 to 20 moles of alkylene oxide, mono- and di-fatty acid esters of ethylene glycol, fatty acid mono glyceride, sorbitan, mono and di-C8-C20 fatty acids, and polyoxyethylene sorbitan and combinations thereof. Alkyl poly glycosides and saccharide fatty amides (e.g. methyl gluconamides) are also suitable nonionic emulsifiers. Preferred nonionic emulsifier is cetyl alcohol and BRIJ 72.

Preferred anionic emulsifiers include alkyl ether sulfate and sulfonates, alkyl sulfates and sulfonates, alkyl benzene sulfonates, alkyl and di alkyl sulfosuccinates, C8-C20 acyl isethionates, C8-C20 alkyl ether phosphates, alkyl ether carboxylates and combinations thereof.

Preferred cationic emulsifiers include palmitamidopropyltrimonium chloride, distearyldimonium chloride and mixtures thereof.

Other generally preferred emulsifiers include glyceryl stearate, glycol stearate, stearamide AMP, PEG-100 stearate as well as emulsifying/thickening additives like hydroxyethylacrylate/sodium acrylyldimethyl taurates copolymer/squalane and mixtures thereof.

The composition of the present invention comprises emulsifiers in amounts from 0.1 to 40 wt %, preferably from 1 to 20 wt %, and more preferably, from 1 to 5 wt %.

Preservatives

Preservatives can be incorporated in the composition to protect against the growth of potentially harmful microorganisms. Illustrative examples of preservatives include methylparaben, ethylparaben, butylparaben, alkyl esters of para-hydroxybenzoic acid, hydantoin, phenoxyethanol, iodopropynyl butyl carbamate, 1,2-octanediol, ethylhexylglycerine, hexylene glycol, imidazolidinyl urea, sodium dehydroacetate and benzyl alcohol. Preferred preservative are methylparaben, phenoxyethanol, iogopropynyl butyl carbamate or mixtures thereof.

The composition of the present invention comprises preservatives in amounts ranging from 0.01 wt % to 2 wt %, preferably from 0.1 to 1 wt %.

Sunscreens

Organic Sunscreens

The composition according to the present invention preferably additionally comprises one or more organic sunscreens. A wide variety of organic sunscreens is suitable for use in compositions of this invention.

Suitable UV-A/UV-B sunscreens include, 2-hydroxy-4-methoxybenzophenone, octyldimethyl p-aminobenzoic acid, digalloyltrioleate, 2,2-dihydroxy-4-methoxybenzophenone, ethyl-4-(bis(hydroxypropyl)) aminobenzoate, 2-ethylhexyl-2-cyano-3,3-diphenylacrylate, 2-ethyihexylsalicylate, glyceryl p-aminobenzoate, 3,3,5-trimethylcyclohexylsalicylate, methylanthranilate, p-dimethyl-aminobenzoic acid or aminobenzoate, 2-ethylhexyl-p-dimethyl-aminobenzoate, 2-phenylbenzimidazole-5-sulfonic acid, 2-(p-dimethylaminophenyl)-5-sulfonicbenzoxazoic acid, 2-ethylhexyl-p-methoxycinnamate, dibenzoylmethance derivatives, 2-hydroxy-4-methoxybenzophenone, octyldimethyl-p-aminobenzoic acid, diethyihexyl naphthylate, Mexoryl, Tinosorb S, Tinosorb M and mixtures thereof.

Preferred dibenzoylmethane derivatives are 4-tert-butyl-4'-methoxydibenzoylmethane, 2-methyldibenzoylmethane, 4-methyl-dibenzoyl-ethane, 4-isopropyldibenzoyl-methane, 4-tert-butyldibenzoylmethane, 2,4-dimethyldibenzoylmethane, 2,5-dimethyldibenzoylmethane, 4,4'-diisopropyl-dibenzoylmethane, 2-methyl-5-isopropyl-4'-methoxydibenzoylmethane, 2-methyl-5-tert-butyl-4'-methoxy-dibenzoyl methane, 2,4-dimethyl-4'-methoxy dibenzoylmethane or 2,6-dimethyl-4-tert-butyl-4'-methoxy-dibenzoylmethane.

Preferred organic sunscreens are 2-ethylhexyl-p-methoxycinnamate (Parsol MCX), dibenzoylmethane derivative; in particular 4-tert.-butyl-4'-methoxydibenzoylmethane (Parsol 1789), 2-ethylhexyl 2-cyano-3,3-diphenyl-2-propenoate (Octocrylene) or mixtures thereof.

An effective amount of organic sunscreens may be used in the compositions of the present invention. The composition preferably comprises from 0.1 to 15 wt %, more preferably from 1 to 10 wt %, most preferably from 2 to 5 wt % organic sunscreens.

Inorganic Sunscreens

The composition may further comprise inorganic sunscreens. Illustrative examples of inorganic sunscreens are zinc oxide, iron oxide, silica, such as fumed silica, or titanium dioxide. Preferred inorganic sunscreens are titanium dioxide (TiO2) and zinc oxide (ZnO).

The composition preferably comprises from 0.1 to 15 wt %, more preferably from 1 to 10 wt %, most preferably from 2 to 5 wt % an inorganic sunscreens.

Additional Actives

A composition as per the present invention may further comprise additional actives.

Illustrative examples of additional actives include 12-hydroxystearic acid, glutathione precursors, galardin, adapalene, aloe extract, ammonium lactate, arbutin, azelaic acid, butyl hydroxy anisole, butyl hydroxy toluene, citrate esters, deoxyarbutin, 1,3 diphenyl propane derivatives, 2,5 dihydroxybenzoic acid and its derivatives, 2-(4-acetoxyphenyl)-1,3 dithane, 2-(4-hydroxyphenyl)-1,3 dithane, ellagic acid, gluco pyranosyl-1-ascorbate, gluconic acid, glycolic acid, green tea extract, 4-Hydroxy-5-methyl-3[2H]-furanone, hydroquinone, 4 hydroxyanisole and its derivatives, 4-hydroxy benzoic acid derivatives, hydroxycaprylic acid, inositol ascorbate, kojic acid, lactic acid, lemon extract, linoleic acid, magnesium ascorbyl phosphate, 5-octanoyl salicylic acid, salicylic acid, 3,4,5 trihydroxybenzyl derivatives, octadecenedioic acid, acetylglucosamine, pitera extract, calcium pantothenate (Melano-block), seppiwhite, soybean extract (bowman birk inhibitor) and mixtures thereof. Preferred actives are 12-hydroxystearic acid, glutathione precursors and galardin.

When incorporated in the composition, an additional active is added preferably from 0.001 to 15 wt %, more preferably from 0.01 to 10 wt % and most preferably from 0.1 to 5 wt %.

DH Adjusters

Conventional buffers/pH adjusters like e.g. sodium hydroxide, potassium hydroxide, hydrochloric acid, citric acid and citrate/citric acid buffers may be used to adjust the pH of the composition of the present invention from 5 to 8, preferably from 6.5 to 7.5.

Optional Cosmetic Ingredients

A composition as per the present invention can comprise a wide range of other optional components. Illustrative examples are antioxidants, binders, biological additives, colorants, polymers, astringents, fragrance, opacifying agents, conditioners, exfoliating agents, natural extracts, essential oils, skin sensates, skin soothing agents, and skin healing agents.

Product Form

A composition according to the present invention is preferably formulated in the form of a powder, flake, tonic, lotion, conditioners, cream, gel or mousse. A composition according to the present invention can be a cosmetic composition for application to skin of mammals, especially humans. Such a cosmetic composition may generally be classified as leave-on or rinse off.

A composition as per the present invention is preferably a leave-on composition.

The Process According to the Present Invention

The process according to the present invention comprises steps (a) to (d) out of which, steps (a) to (c) may be carried out in any particular order. For example, a compound selected from resorcinol, PER, 4-alkyl substituted resorcinol and mixtures thereof may be combined with a chelating agent in water and kept aside until cosmetically acceptable base of step (c) is prepared. Alternatively, step (a) may be carried out after the cosmetically acceptable base of step (c) is ready. Within step (b) too, preparation of water phase and oil phase may be carried out in no particular order.

According to the present invention, it is required that a compound selected from resorcinol, PER, 4-alkyl substituted resorcinol and mixtures thereof is combined with a chelating agent in water; before such selected compound is combined with cosmetically acceptable base in step (d).

Step (a): Combining a compound selected from resorcinol, PER, 4-alkyl substituted resorcinol and mixtures thereof with a chelating agent.

In step (a), a compound selected from resorcinol, PER, 4-alkyl substituted resorcinol and mixtures thereof is combined with a chelating agent in water. As used herein, "combining" may simply mean mixing.

In addition to water, polyols like glycerol, propylene glycol, butylene glycol or mixtures thereof, may be used to enhance solubility of a compound selected from resorcinol, PER, 4-alkyl substituted resorcinol and mixtures thereof in water. When used, polyols are preferably mixed with water and then a compound selected from resorcinol, PER, 4-alkyl substituted resorcinol and mixtures thereof and a chelating agent were added to such mixture. Polyol like e.g. butylene glycol is preferably added in a ratio 1:8 with water, more preferably 1:6 and most preferably 1:4, with water. For example, in case of HR, 20 parts of butylene glycol were first mixed with 80 parts of water. To this mixture of water and butylene glycol, HR and a chelating agent were added. In case of ER, solubility enhancing polyols may or may not be used.

Step (a) is preferably carried out at room temperature.

The adduct obtained in this step may be kept ready for addition to the cosmetically acceptable base. Alternatively, step (a) may be carried out when cosmetically acceptable base of step (c) is ready.

Steps (b): Preparing water and oil phases.

Cosmetically acceptable base according to the present invention is prepared by combining water and oil phases.

Water phase is prepared by heating water to a temperature range preferably from 60 to 85° C., more preferably from 65 to 80° C. and most preferably from 70 to 75° C. Ingredients that are suitable to be added in water phase may be added in this step and can be homogenized preferably up to 30 minutes, more preferably up to 20 minutes and most preferably up to 10 minutes so that all the ingredients are melted.

Oil Phase is prepared by heating oil to a temperature ranging preferably from 60 to 85° C., more preferably from 65 to 80° C. and most preferably from 70 to 75° C. Ingredients that are suitable to be added in oil phase may be added in this step and can be homogenized preferably for up to 30 minutes, more preferably up to 20 minutes and most preferably up to 10 minutes so that all the ingredients are melted.

Step (c): Combining water and oil phases.

Oil phase is then added to water phase preferably when the temperature is in the range from 60 to 85° C., more preferably from 65 to 80° C. and most preferably from 70 to 75° C. with proper homogenizing carried out preferably up to 30 minutes, more preferably up to 20 minutes and most preferably up to 10 minutes.

Step (d): Mixing adduct of step (a) with the cosmetically acceptable base of step (c).

The cosmetically acceptable base obtained in step (c) is cooled down to a temperature that is suitable for addition of the adduct obtained in step (a). Temperature range that is suitable for carrying out step (d) is preferably from 30 to 60° C., more preferably from 35 to 55° C. and most preferably from 40 to 45° C. After combining the adduct of step (a) with the cosmetically acceptable base, proper mixing is carried out preferably up to 30 minutes, more preferably up to 20 minutes and most preferably up to 10 minutes. The batch was then cooled down to room temperature.

The difference between the process of the present invention and known processes for preparing cosmetic compositions is that, in the process as per the present invention, a compound selected from resorcinol, PER, 4-alkyl substituted resorcinol and mixtures thereof are combined with a chelating agent before resorcinol or PER or 4-alkyl substituted resorcinol or mixtures thereof are added to the cosmetically acceptable base or brought in contact with any other ingredient that may be present in the composition.

Whereas, in known processes, resorcinol or PER or 4-alkyl substituted resorcinol or mixtures thereof are not combined with a chelating agent before adding them to a cosmetically acceptable base or brought in contact with any other ingredient that may be present in a composition. That is to say, resorcinol or PER or 4-alkyl substituted resorcinol or mixtures thereof and chelating agents are always present in different phases of preparing the compositions and do not beforehand interact with each other.

Without wishing to be bound by theory it is believed that in the process as per the present invention, the two ingredients interact with each other in a specific way. As a result, compositions made as per the process of the present invention show enhanced color stability compared to that of compositions made as per known process. However, enhanced color stability is not obtained when HR is used in combination with EDDS.

While the exact nature of the interaction between the two ingredients is not fully understood. It is believed that such interaction is not through already known metal chelating effect of chelating agents. When simple water solution of resorcinol or PER or 4-alkyl substituted resorcinol made with or without a chelating agent were stored at 45° C. for 7 days, it was found that solutions that contained a chelating agent, showed lesser color change as compared to the solutions which did not contain a chelating agent. Importantly, these water solutions were found to contain less than 2 ppm of metals like e.g. iron, calcium and zinc when assayed for its metal content.

For assessing color stability, color change ($\Delta E$) was calculated based on the color measurement presented by Hunter lab color space L* a* and b* where, L* is black-white space, a* is green-red space, b* is blue-yellow space. For example, larger L* value means more white, and smaller b* value means more blue. Lower the value of $\Delta E$, lower is reduction in color change, i.e. increased color stability.

Images of water solutions mentioned above were captured at time zero, i.e. just after they are made and at the end of the storage period, i.e. at the end of 4 weeks. All images were converted to L*, a* and b* data using Hunter lab-lab scan XE instrument. The values of L*, a* and b* at week 4 and week zero (initial data) were used to calculate ΔE using the formula:

$$\Delta E = \sqrt{(L_2^* - L_1^*)^2 + (a_2^* - a_1^*)^2 + (b_2^* - b_1^*)^2}$$

Further, it was also found that, post-addition of a chelating agent did not reverse color developed due to loss of color stability of a compound selected from resorcinol, PER, 4-alkyl substituted resorcinol and mixtures thereof in compositions prepared as per comparative process. Therefore, combining a compound selected from resorcinol, PER, 4-alkyl substituted resorcinol and mixtures thereof with a chelating agent as per the process of the present invention was found to be crucial as color stability was exhibited only when process as per the present invention was carried out.

The invention is further described using following non-limiting examples.

EXAMPLES

Example 1 (Comparative Example)

Comparative compositions A to D were prepared as per the process described below, a process not according to the present invention. Compositional details are as shown in Table 1.

Step 1: Dissolving a Compound Selected from Resorcinol, PER, 4-Alkyl Substituted Resorcinol and Mixtures Thereof in a Solvent.

ER or HR was dissolved in water at room temperature.

Step 2: Preparing Water and Oil Phases.

Water phase is prepared by heating water at at 75° C. and a chelating agent, i.e. EDTA or EDDS, was dissolved in it with proper mixing carried out for 10 minutes.

Oil phase was prepared by heating 12 wt % stearic acid at 75° C. To this, 0.4 wt % Parsol 1789, 0.75 wt % ethyihexyl methoxycinnamate, 0.7 wt % titanium dioxide and 0.25 wt % tocopheryl acetate were added and the mix was homogenized for 10 minutes.

Step 3: Combining Water and Oil Phases.

The oil phase was then added to the water phase and the mixture was homogenized at 75° C. for 10 minutes.

Step 4: Mixing Product of Step 1 with Cosmetically Acceptable Base of Step 4.

The cosmetically acceptable base obtained in step 3 was cooled down to 45° C. and product of step 1 was combined with it by proper mixing carried out for 10 minutes. The batch was then cooled down to room temperature.

Example 2

Compositions 1 to 4 were prepared as per the process of the present invention as described below. Compositional details are given in table 1.

Step (a):

0.25 wt % HR was combined with 0.1 wt % EDTA in mixture of 1 wt % water and 1 wt % glycerol, at room temperature in a container. Such mixture was mixed until HR and EDTA were completely dissolved in water and glycerol.

Step (b):

Water was heated at 75° C. and 0.2% methylparaben, 0.91 wt % potassium hydroxide were dissolved in it. This mixture was kept stirring in a container and an oil phase was prepared as follows.

Oil phase was prepared by heating 12 wt % stearic acid at 75° C. To this, 0.4 wt % Parsol 1789, 0.75 wt % ethyihexyl methoxycinnamate, 0.7 wt % titanium dioxide and 0.25 wt % tocopheryl acetate were added and the mix was homogenized for 10 minutes.

Step (c):

Water and oil phases were combined by adding oil phase in to water phase followed by homogenizing it at 75° C. for 10 minutes to obtain cosmetically acceptable base.

Step (d):

After the emulsion obtained in step (c) was cooled to 45° C., entire adduct obtained in step (a) was combined with the cosmetically acceptable base and was mixed until uniform. The batch was then cooled down to room temperature.

TABLE 1

Compositional details for examples A to D and 1 to 4 (wt %)

| Ingredient | A/1 | B/2 | C/3 | D/4 |
| --- | --- | --- | --- | --- |
| Stearic acid | 12 | 12 | 12 | 12 |
| Sunscreens | 1.85 | 1.85 | 1.85 | 1.85 |
| Vitamin E acetate | 0.1 | 0.1 | 0.1 | 0.1 |
| Vitamin B3 | 1.25 | 1.25 | 1.25 | 1.25 |
| Vitamin B6 | 0.01 | 0.01 | 0.01 | 0.01 |
| EDTA | 0.1 | — | 0.1 | — |
| EDDS | — | 0.1 | — | 0.1 |
| Hexyl Resorcinol | 0.25 | 0.25 | — | — |
| Ethyl Resorcinol | — | — | 0.25 | 0.25 |
| Glycerine | 1 | 1 | 1 | 1 |
| Methyl paraben | 0.2 | 0.2 | 0.2 | 0.2 |
| Phenoxyethanol | 0.4 | 0.4 | 0.4 | 0.4 |
| Hydroxystearic acid | 0.1 | 0.1 | 0.1 | 0.1 |
| Potassium hydroxide | 0.41 | 0.41 | 0.41 | 0.41 |
| Perfume | 0.35 | 0.35 | 0.35 | 0.35 |
| Water | To 100 | To 100 | To 100 | To 100 |

Color Stability of Compositions

For assessing color stability, ΔE of all the compositions, i.e. A to D and 1 to 4, was calculated. All the samples were stored for 4 weeks in 2 oz. glass jars at a temperature from 45 to 50° C. All samples were loaded in Hunter Lab XE measurement cell at time zero, i.e. just after they are made and at the end of 4 weeks of storage and color data were collected directly from the instrument. The values of L*, a* and b* at week 4 and week zero (initial data) were used to calculate ΔE using the formula previously provided. ΔE of all the compositions is given in table 2 below.

TABLE 2

Color stability of HR and ER in composition

| Compo-sition | Active + Chelating agent | Week 0 Color | | | Week 4 Color | | | ΔE |
| --- | --- | --- | --- | --- | --- | --- | --- | --- |
| | | L* | a* | b* | L* | a* | b* | |
| A | HR + EDTA | 87.16 | 8.6 | 5.3 | 84.5 | 9.96 | 11.9 | 7.24 |
| 1 | HR + EDTA | 84.69 | 10.33 | 6.36 | 83.15 | 10.96 | 11.23 | 5.15 |
| B | HR + EDDS | 83.86 | 9.36 | 6.68 | 79.7 | 12.65 | 18.32 | 12.79 |
| 2 | HR + EDDS | 84.93 | 9.01 | 6.56 | 79.55 | 12.99 | 25.68 | 20.26 |
| C | ER + EDTA | 86.31 | 8.71 | 6.06 | 79.93 | 23.29 | 52.68 | 49.26 |
| 3 | ER + EDTA | 85.52 | 9.2 | 6.17 | 80.15 | 21.75 | 49.64 | 45.56 |
| D | ER + EDDS | 84.69 | 9.29 | 6.25 | 74.67 | 22.98 | 54.61 | 51.25 |
| 4 | ER + EDDS | 83.87 | 10.35 | 6.3 | 76.07 | 17.36 | 44.13 | 39.26 |

As seen from the data in table 2, color stability of HR is improved when a chelating agent other than EDDS is used whereas color stability of ER is improved when any one of the chelating agents EDTA or EDDS is used.

The invention claimed is:

1. A process for preparing a cosmetic composition comprising:
   (a) preparing, separately, a water phase and an oil phase;
   (b) emulsifying the water phase and the oil phase to prepare a cosmetically acceptable base;
   (c) preparing an adduct by combining a compound selected from resorcinol, phenylethyl resorcinol, 4-alkyl substituted resorcinol and mixtures thereof with a chelating agent in water; and
   (d) combining the adduct obtained in step (c) with the cosmetically acceptable base of step (b),
   wherein the process does not comprise a combination of 4-hexyl resorcinol with ethylenediamine di-succinic acid; and
   wherein the cosmetic composition is applied to skin.

2. The process according to claim 1, wherein 4-alkyl-substituted esorcinol is selected from 4-methyl resorcinol, 4-ethyl resorcinol, 4-propyl resorcinol, 4-isopropyl resorcinol, 4-butyl resorcinol, 4-pentyl resorcinol, 4-hexyl resorcinol, 4-heptyl resorcinol, 4-octyl resorcinol and mixtures thereof.

3. The process according to claim 1, wherein the chelating agent is selected from ethylenediamine tetra-acetic acid, ethylenediamine di-succinic acid and mixtures thereof.

4. The process according to claim 1, wherein the adduct of step (c) is selected from 4-hexyl resorcinol+ethylene diamine tetra acetic acid, 4-ethyl resorcinol+ethylene diamine tetra acetic acid and 4-ethyl resorcinol+ethylene diamine disuccinic acid.

5. The process according to claim 1, wherein step (d) is carried out when the temperature of the cosmetically acceptable base obtained in step (b) is in the range from 40 to 50° C.

6. The process according to claim 1, wherein the water phase in step (a) is prepared by dissolving water phase ingredients in water that has temperature from 60 to 80° C.

7. The process according to claim 1, wherein the water phase comprises a vitamin, glycerin and a surfactant.

8. The process according to claim 1, wherein the oil phase in step (a) is prepared by dissolving oil phase ingredients in oil that has temperature from 60 to 80° C.

9. The process according to claim 1, wherein the oil phase comprises a surfactant and a sunscreen.

10. A process for preparing a cosmetic composition wherein, the process consists essentially of:
    (a) preparing a water phase comprising heating water to a temperature range of from 65 to 80° C.;
    (b) preparing an oil phase comprising dissolving oil phase ingredients in oil that has temperature from 65 to 80° C.;
    (c) emulsifying the water phase and the oil phase to prepare a cosmetically acceptable base;
    (d) preparing an adduct by mixing in water at room temperature a 4-alkyl substituted resorcinol with a chelating agent selected from ethylenediamine tetra-acetic acid or ethylenediamine di-succinic acid; and
    (e) combining the adduct obtained in step (d) with the cosmetically acceptable base of step (c) when the temperature of said cosmetically acceptable base is from 40 to 45° C.
    wherein the adduct of step (d) is selected from 4-hexyl resorcinol+ethylene diamine tetra acetic acid, 4-ethyl resorcinol+ethylene diamine tetra acetic acid and 4-ethyl resorcinol+ethylene diamine disuccinic acid; and
    wherein the cosmetic composition is applied to skin.

* * * * *